United States Patent [19]

Danielson

[11] Plant 4,092

[45] Aug. 16, 1977

[54] CHRYSANTHEMUM PLANT NAMED COPPER HOSTESS

[75] Inventor: Robert E. Danielson, West Chicago, Ill.

[73] Assignee: Pan American Plant Company, West Chicago, Ill.

[21] Appl. No.: 731,743

[22] Filed: Oct. 12, 1976

[51] Int. Cl.[2] ..... A01H 5/00

[52] U.S. Cl. ..... Plt./79

[58] Field of Search ..... Plt./79

*Primary Examiner*—Robert E. Bagwill

*Attorney, Agent, or Firm*—Chas. W. Rummler

[57] ABSTRACT

A new variety of chrysanthemum plant of the pot-plant type for greenhouse culture distinguished by the orange-bronze coloring of its medium size blooms, good breaking ability, a dependable 9-week response, and the ability to be flowered year around under proper photoperiod control.

1 Drawing Figure

BACKGROUND OF THE NEW PLANT

This chrysanthemum originated as a sport of the cultivar Hostess (U.S. Plant Pat. No. 3,224) and was discovered by me among greenhouse plants of the parent variety growing at West Chicago, Ill. Asexual propagation of this sport was done by me, by cuttings from the original plant, at West Chicago, Ill., and successive generations of this new plant propagated by vegetative cuttings have demonstrated that its distinctive characteristics hold true from generation to generation and appear to be firmly fixed.

DESCRIPTION OF THE DRAWING

My new variety of chrysanthemum is illustrated by the accompanying drawing which shows the potted plant in full bloom and in full color, as nearly true as it is possible to obtain by conventional photographic procedures, and the inked drawn figures show the configuration of typical specimens of mature, mid-term, and young leaves of the new plant.

DESCRIPTION OF THE NEW PLANT

The following is a detailed description of my new variety of chrysanthemum plant with color identification according to the RHS Colour Chart published by the Royal Horticultural Society of London, England, in collaboration with The British Colour Council.

THE PLANT

Origin: Sport.

Parentage: Hostess, U.S. Plant Pat. No. 3,224.

Classification:

*Botanic.*—Chrysanthemum morifolium.

*Commercial.*—Greenhouse pot plant.

Form: Perennial herbaceous bush.

Height: 11 to 13 inches.

Growth: Terminal. Vigorous and upright, with good strength and sturdiness.

Branching: Normal under natural conditions.

Foliage: Quantity — abundant, with about eight to 10 leaves per 4 inches of stem.

*Leaf size.*—3 to 4½ inches long and 2 to 2½ inches wide.

*Shape.*—Lobed and slightly serrated.

*Appearance.*—Canescent.

*Color.*—Upper side — Green 147A. Under side — Green 137C.

*Venation.*—Pinnately.

*Petioles.*—½ to ⅝ inch long.

THE BUD

Form: Almost global.

Size: ½ to ⅝ inch in diameter; ¼ to ⅜ inch in depth.

Opening: Bud opens slowly.

Color:

*When phyllaries first divide.*—Green 154B.

*When florets begin to unfurl.*—Greyed Red 180A.

Phyllaries: Spear shaped and upstanding. The outline of the receptacle bears many involucral bracts.

*Color:*—Inside — Green 138A. Outside — Green 137B.

*Surface texture.*—Pubescent.

Peduncle: ⅝ to ¾ inch long, erect and with pubescent surface.

THE FLOWER

Blooming characteristic: The plant can be flowered year around with photoperiod control.

Response: Dependable 9 week.

Natural Season: October 27 to November 5.

Flower Type: Composite and decorative.

Size of Bloom: Medium (disbudded).

*Diameter.*—3½ to 4½ inches.

*Depth.*—2 to 2½ inches.

Borne: As a head of many florets on a receptacle.

Shape: Cup shaped when bloom first opens, changing to a generally hemispherical shape as bloom matures.

Florets: Numerous.

*Color.*—Outer florets:

Flowering Season

| | January | July |
|---|---|---|
| Upper side - | Greyed Orange 170A | Greyed Orange 168A |
| Reverse - | Greyed Orange 168C | Greyed Orange 167B |
| Inside florets: | | |
| Upper side- | Greyed Orange 169A | Greyed Orange 171A |
| Reverse - | Greyed Orange 168A | Greyed Orange 172C |

*Texture.*—Medium firmness.

*Appearance.*—Very slight shine.

Discoloration: Very slight fade after full bloom.

Persistence: The flower and its florets hang on and dry.

Lasting Quality:

*On plant.*—3 weeks.

*As cut flower.*—Not recommended.

REPRODUCTIVE ORGANS

Stamens: Number — 5 syngeneious.

*Arrangement.*—Connate by the anthers to form a cylinder about the style.

*Filament.*—1/16 to ⅛ inch long. Color: Light yellow. Pollen: Yellow in color.

Pistils: One to each ray floret.

*Styles.*—⅛ to 3/16 inch long.

*Stigmas.*—Color — Yellow.

Ovaries: Inferior bicarpellate.

This new variety of chrysanthemum plant is very similar to its parent cultivar Hostess (U.S. Plant Pat. No. 3,224) in relation to its compact growth habit, its good breaking ability, i.e., 4 to 6 lateral breaks when manually pinched, its dense dark green foliage, dependable nine-week response and the ability to be flowered year around at West Chicago, Ill. The new plant is, however, very distinctive from its parent in flower color, by less longitudinal petal roll and less reflexing of the outer ray florets, and by its larger flower size.

I claim:

1. A new and distinct variety of chrysanthemum plant, substantially as herein shown and described, characterized particularly, when compared to its parent "Hostess", by its unique orange-bronze coloration, less longitudinal petal roll and less reflexing of the outer ray florets, and by its larger flower size.

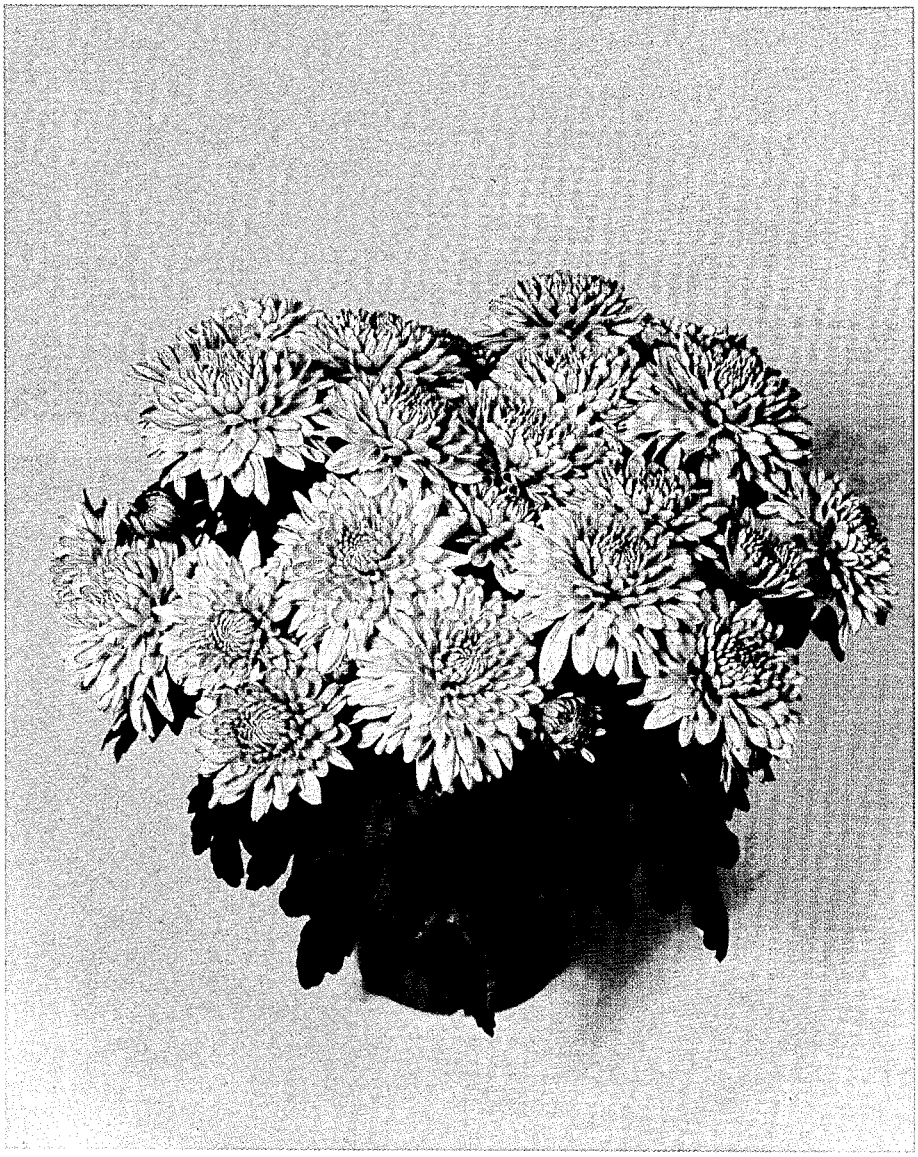
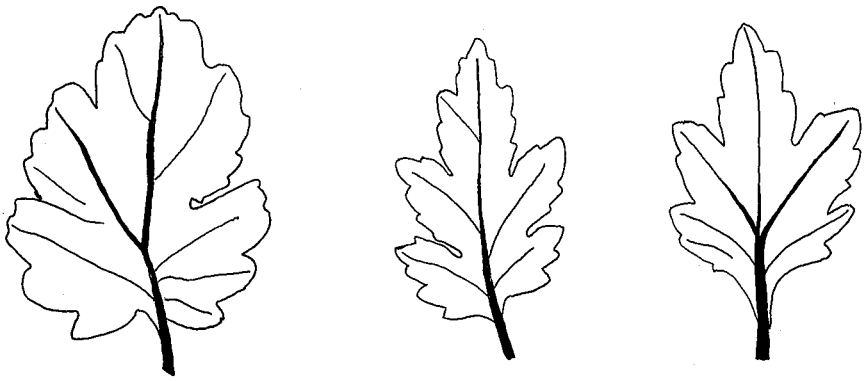

* * * * *